US005965401A

United States Patent [19]
Chang et al.

[11] Patent Number: 5,965,401
[45] Date of Patent: Oct. 12, 1999

[54] PURIFIED MAMMALIAN NK ANTIGENS AND RELATED REAGENTS

[75] Inventors: Chiwen Chang, San Jose; Lewis L. Lanier, Los Altos; Joseph H. Phillips, Jr., San Carlos, all of Calif.

[73] Assignee: Schering Corporation, Kenilworth, N.J.

[21] Appl. No.: 08/738,462

[22] Filed: Oct. 24, 1996

Related U.S. Application Data

[63] Continuation of application No. 08/093,435, Jul. 16, 1993, abandoned.

[51] Int. Cl.$^6$ ............................ C12P 21/06; G01N 33/53; C07K 2/00; C07K 16/00
[52] U.S. Cl. ............................ 435/69.3; 435/7.1; 435/7.2; 514/12; 536/23.1; 536/23.4; 530/300; 530/350; 530/387.1; 530/388.9; 530/388.1
[58] Field of Search .......................... 435/7.1, 7.2, 69.3; 514/12; 536/23.1, 23.4; 530/300, 350, 387.1, 388.9, 388.1

[56] References Cited

U.S. PATENT DOCUMENTS

| | | |
|---|---|---|
| 5,124,251 | 6/1992 | Lanier et al. ............................ 435/7.21 |
| 5,811,284 | 9/1998 | Chang et al. . |

OTHER PUBLICATIONS

Wayne M. Yokoyama, "Recognition structures on natural killer cells," *Current Opinion in Immunology.*, 5:67–73, 1993.
William H. Chambers, et al., "Type II integral membrane proteins with characteristics of C–type animal lectins expressed by natural killer (NK) cells," *Glycobiology*, 3(1):9–14, 1993.
Hisashi Arase, et al., "An NK1.1$^+$ CD4$^+$8$^-$ Single–Positive Thymocyte Subpopulation That Expresses a Highly Skewed T–cell Antigen Receptor V$_\beta$ Family," *Proc. Natl. Acad. Sci. USA*, vol. 89, pp. 6506–6510, Jul. 1992.
Zuhair K. Ballas, et al., "NK1.1$^+$ Thymocytes: Adult Murine CD4$^-$, CD8$^-$ Thymocytes Contain an NK1.1$^+$, CD3$^+$, CD5$^{hi}$, CD44$^{hi}$, TCR–V$\beta$8$^+$ Subset," *J. Immunol.*, vol. 145, No. 4, pp. 1039–1045, Aug. 1990.
William H. Chambers, et al., "Monoclonal Antibody to a Triggering Structure Expressed on Rat Natural Killer Cells and Adherent Lymphokine–Activated Killer Cells," *J. Exp. Med.*, vol. 169, pp. 1373–1389, Apr. 1989.
Genbank Sequences: Mouse NKR–P1A, Mouse NKR–P1B, Mouse NKR–P1C, and Rat NKAAA.
Roberto Giorda, et al., "Genomic Structure and Strain–Specific Expression of the Natural Killer Cell Receptor NKR–P1," *J. Immunol.*, vol. 149, No. 6, pp. 1957–1963, Sep. 1992.

Roberto Giorda, et al., "Mouse NKR–P1: A Family of Genes Selectively Coexpressed in Adherent Lymphokine–Activated Killer Cells," *J. Immunol.*, vol. 147, No. 5, pp. 1701–1708, Sep. 1991.
Roberto Giorda, et al., "NKR–P1, a Signal Transduction Molecule on Natural Killer Cells," *Science*, vol. 249, pp. 1298–1300, Sep. 1990.
Franz M. Karlhofer, et al., "Stimulation of Murine Natural Killer (NK) Cells by a Monoclonal Antibody Specific for the NK1.1 Antigen," *J. Immunol.* vol. 146, No. 10, pp. 3662–3673, May 1991.
Klas Kärre, et al., "Multiple Interactions at the Natural Killer Workshop," *Immunology Today*, vol. 12, No. 10, pp. 343–345, 1991.
Gloria C. Koo, et al., "Establishment of Monoclonal Anti–Nk–1.1 Antibody," *Hybridoma*, vol. 3, No. 3, pp. 301–303, 1984.
E. C. Niemi, et al., "Mutational Loss of NKR–P1 from RNK–16 Cells Is Accompanied by Loss of Cytotoxicity Against YAC–1 Targets," *Natural Immunity and Cell Growth Regulation*, vol. 10, pp. 146–147, 1991.
James C. Ryan, et al., "Molecular Cloning of the NK1.1 Antigen, a Member of the NKR–P1 Family of Natural Killer Cell Activation Molecules," *J. Immunol.*, vol. 149, No. 5, pp. 1631–1635, Sep. 1992.
James C. Ryan, et al., "NKR–P1, an Activating Molecule on Rat Natural Killer Cells, Stimulates Phosphoinositide Turnover and a Rise in Intracellular Calcium," *J. Immunol.*, vol. 147, No. 9, pp. 3244–3250, Nov. 1991.
Charles L. Sentman, et al., "Pan Natural Killer Cell Monoclonal Antibodies and Their Relationship to the NK1.1 Antigen," *Hybridoma*, vol. 8, No. 6, pp. 605–614, 1989.
Wayne M. Yokoyama, et al., "cDNA Cloning of Mouse NKR–P1 and Genetic Linkage with LY–49: Identification of a Natural Killer Cell Gene Complex on Mouse Chromosome 6," *J. Immunol.*, vol. 147, No. 9, pp. 3229–3236, Nov. 1991.
Wayne M. Yokoyama, "The Ly–49 and NKR–P1 Gene Families Encoding Lectin–Like Receptors on Natural Killer Cells: The NK Gene Complex," *Annu. Rev. Immunol.*, vol. 11, pp. 613–635, 1993.
Lanier et al J. Immunol. 149(6): 1876–80, 1992.
Lanier et al J. Immunol 146(12): 4421–4426, 1991.
Lewin, Science 237:1570, 1987.
Reeck et al, Cell 50:667, 1987.

*Primary Examiner*—Nita Minnifield
*Attorney, Agent, or Firm*—Sheela Mohan-Peterson; Edwin P. Ching

[57] ABSTRACT

NK cell surface antigen from a mammal, reagents related thereto including purified proteins, specific antibodies, and nucleic acids encoding this antigen. Methods of using those reagents and diagnostic kits are also provided.

28 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 738 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 61..738

(xi) SEQUENCE DESCRIPTION: SEQ ID NO:1:

```
AAAGCAGAAT TGAGAGTTTG TTCTTACACA CAAGTTTAAT GCCACCTTCC TCTGTCTGCC        60

ATG GAC CAA CAA GCA ATA TAT GCT GAG TTA AAC TTA CCC ACA GAC TCA        108
Met Asp Gln Gln Ala Ile Tyr Ala Glu Leu Asn Leu Pro Thr Asp Ser
 1               5                  10                  15

GGC CCA GAA AGT TCT TCA CCT TCA TCT CTT CCT CGG GAT GTC TGT CAG        156
Gly Pro Glu Ser Ser Ser Pro Ser Ser Leu Pro Arg Asp Val Cys Gln
             20                  25                  30

GGT TCA CCT TGG CAT CAA TTT GCC CTG AAA CTT AGC TGT GCT GGG ATT        204
Gly Ser Pro Trp His Gln Phe Ala Leu Lys Leu Ser Cys Ala Gly Ile
         35                  40                  45

ATT CTC CTT GTC TTG GTT GTT ACT GGG TTG AGT GTT TCA GTG ACA TCC        252
Ile Leu Leu Val Leu Val Val Thr Gly Leu Ser Val Ser Val Thr Ser
     50                  55                  60

TTA ATA CAG AAA TCA TCA ATA GAA AAA TGC AGT GTG GAC ATT CAA CAG        300
Leu Ile Gln Lys Ser Ser Ile Glu Lys Cys Ser Val Asp Ile Gln Gln
 65                  70                  75                  80
```

```
AGC AGG AAT AAA ACA ACA GAG AGA CCG GGT CTC TTA AAC TGC CCA ATA        348
Ser Arg Asn Lys Thr Thr Glu Arg Pro Gly Leu Leu Asn Cys Pro Ile
             85                  90                  95

TAT TGG CAG CAA CTC CGA GAG AAA TGC TTG TTA TTT TCT CAC ACT GTC        396
Tyr Trp Gln Gln Leu Arg Glu Lys Cys Leu Leu Phe Ser His Thr Val
            100                 105                 110

AAC CCT TGG AAT AAC AGT CTA GCT GAT TGT TCC ACC AAA GAA TCC AGC        444
Asn Pro Trp Asn Asn Ser Leu Ala Asp Cys Ser Thr Lys Glu Ser Ser
            115                 120                 125

CTG CTG CTT ATT CGA GAT AAG GAT GAA TTG ATA CAC ACA CAG AAC CTG        492
Leu Leu Leu Ile Arg Asp Lys Asp Glu Leu Ile His Thr Gln Asn Leu
        130                 135                 140

ATA CGT GAC AAA GCA ATT CTG TTT TGG ATT GGA TTA AAT TTT TCA TTA        540
Ile Arg Asp Lys Ala Ile Leu Phe Trp Ile Gly Leu Asn Phe Ser Leu
145                 150                 155                 160

TCA GAA AAG AAC TGG AAG TGG ATA AAC GGC TCT TTT TTA AAT TCT AAT        588
Ser Glu Lys Asn Trp Lys Trp Ile Asn Gly Ser Phe Leu Asn Ser Asn
            165                 170                 175

GAC TTA GAA ATT AGA GGT GAT GCT AAA GAA AAC AGC TGT ATT TCC ATC        636
Asp Leu Glu Ile Arg Gly Asp Ala Lys Glu Asn Ser Cys Ile Ser Ile
            180                 185                 190

TCA CAG ACA TCT GTG TAT TCT GAG TAC TGT AGT ACA GAA ATC AGA TGG        684
Ser Gln Thr Ser Val Tyr Ser Glu Tyr Cys Ser Thr Glu Ile Arg Trp
        195                 200                 205

ATC TGC CAA AAA GAA CTA ACA CCT GTG AGA AAT AAA GTG TAT CCT GAC        732
Ile Cys Gln Lys Glu Leu Thr Pro Val Arg Asn Lys Val Tyr Pro Asp
        210                 215                 220

TCT TGA                                                                738
Ser
225

(2) INFORMATION FOR SEQ ID NO:2:

(i) SEQUENCE CHARACTERISTICS:
        (A) LENGTH: 225 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Gln Gln Ala Ile Tyr Ala Glu Leu Asn Leu Pro Thr Asp Ser
 1               5                  10                  15

Gly Pro Glu Ser Ser Pro Ser Ser Leu Pro Arg Asp Val Cys Gln
            20                  25                  30

Gly Ser Pro Trp His Gln Phe Ala Leu Lys Leu Ser Cys Ala Gly Ile
        35                  40                  45

Ile Leu Leu Val Leu Val Val Thr Gly Leu Ser Val Ser Val Thr Ser
     50                  55                  60

Leu Ile Gln Lys Ser Ser Ile Glu Lys Cys Ser Val Asp Ile Gln Gln
65                  70                  75                  80

Ser Arg Asn Lys Thr Thr Glu Arg Pro Gly Leu Leu Asn Cys Pro Ile
            85                  90                  95

Tyr Trp Gln Gln Leu Arg Glu Lys Cys Leu Leu Phe Ser His Thr Val
           100                 105                 110

Asn Pro Trp Asn Asn Ser Leu Ala Asp Cys Ser Thr Lys Glu Ser Ser
           115                 120                 125

Leu Leu Leu Ile Arg Asp Lys Asp Glu Leu Ile His Thr Gln Asn Leu
        130                 135                 140
```

```
-continued

Ile Arg Asp Lys Ala Ile Leu Phe Trp Ile Gly Leu Asn Phe Ser Leu
145                 150                 155                 160

Ser Glu Lys Asn Trp Lys Trp Ile Asn Gly Ser Phe Leu Asn Ser Asn
                165                 170                 175

Asp Leu Glu Ile Arg Gly Asp Ala Lys Glu Asn Ser Cys Ile Ser Ile
            180                 185                 190

Ser Gln Thr Ser Val Tyr Ser Glu Tyr Cys Ser Thr Glu Ile Arg Trp
        195                 200                 205

Ile Cys Gln Lys Glu Leu Thr Pro Val Arg Asn Lys Val Tyr Pro Asp
        210                 215                 220

Ser
225
```

PURIFIED MAMMALIAN NK ANTIGENS AND RELATED REAGENTS

This application is a continuation of application Ser. No. 08/093,435 filed Jul. 16, 1993 now abandoned.

FIELD OF THE INVENTION

The present invention relates to compositions related to proteins which function in controlling physiology, development, and differentiation of mammalian cells, e.g., cells of a mammalian immune system. In particular, it provides proteins and mimetics which regulate cellular physiology, development, differentiation, or function of various cell types, including hematopoietic cells, and particularly natural killer (NK) and T cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow, T cells, which were originally characterized as differentiating in the thymus, and natural killer (NK) cells. See, e.g., Paul (ed.) (1989) *Fundamental Immunology* (2d ed.) Raven Press, New York.

In many aspects of the development of an immune response or cellular differentiation, soluble proteins, e.g., cytokines, and cell surface antigens, e.g., CD markers, play critical roles in regulating cellular interactions. These cytokines and cell markers apparently mediate cellular activities in many ways. They have been shown, in many cases, to modulate proliferation, growth, and differentiation of hematopoietic stem cells into the vast number of progenitors composing the lineages responsible for an immune response.

However, the cellular molecules which are expressed by different developmental stages of cells in these maturation pathways are still incompletely identified. Moreover, the roles and mechanisms of action of signaling molecules which induce, sustain, or modulate the various physiological, developmental, or proliferative states of these cells is poorly understood. Clearly, the immune system and its response to various stresses have relevance to medicine, e.g., infectious diseases, cancer related responses and treatment, allergic and transplantation rejection responses. See, e.g., Thorn et al. *Harrison's Principles of Internal Medicine* McGraw/Hill, New York.

Medical science relies, in large degree, to appropriate recruitment or suppression of the immune system in effecting cures for insufficient or improper physiological responses to environmental factors. However, the lack of understanding of how the immune system is regulated or differentiates has blocked the ability to advantageously modulate the normal defensive mechanisms to biological challenges. Medical conditions characterized by abnormal or inappropriate regulation of the development or physiology of relevant cells thus remain unmanageable. The discovery and characterization of specific cytokines and markers, e.g., involved in cell—cell interactions, will contribute to the development of therapies for a broad range of degenerative or other conditions which affect the immune system, hematopoietic cells, as well as other cell types. The present invention provides solutions to some of these and many other problems.

SUMMARY OF THE INVENTION

The present invention is based, in part, upon the discovery of a cDNA clone encoding a member of a family of cell surface markers, initially characterized on natural killer (NK) and T cells and designated DX1. The invention embraces isolated genes encoding the proteins of the invention, variants of the encoded proteins, e.g., mutations (muteins) of the natural sequence, species and allelic variants, fusion proteins, chemical mimetics, antibodies, and other structural or functional analogues. Various uses of these different nucleic acid or protein compositions are also provided.

The present invention provides nucleic acids encoding a DX1 protein or fragment thereof; a substantially pure DX1 or peptide thereof, or a fusion protein comprising DX1 sequence; and an antibody raised to a DX1 protein.

In nucleic acid embodiments, the nucleic acid can comprise a sequence of Table 1.

In substantially pure DX1 protein or peptide thereof embodiments, the protein or peptide can be from a primate, including a human; comprise at least one polypeptide segment of Table 1; or exhibit a post-translational modification pattern distinct from natural DX1 protein. A further embodiment is a composition comprising such a protein and a pharmaceutically acceptable carrier.

In antibody embodiments, the antigen can be a primate protein, including a human; the antibody is raised against a protein sequence of Table 1; the antibody is a monoclonal antibody; or the antibody is labeled.

The invention also embraces a kit comprising a substantially pure nucleic acid encoding a DX1 protein or peptide; a substantially pure DX1 protein or fragment, e.g., as a positive control; or an antibody or receptor which specifically binds a DX1 protein.

Methods for screening for ligands or other proteins which specifically bind to DX1 are also provided.

The availability of these reagents also provides methods of modulating physiology or development of a cell comprising contacting said cell with an agonist or antagonist of a DX1 protein. For example, the antagonist might be an antibody against a mammalian DX1 protein or the cell may be a hematopoietic cell, including a lymphoid cell.

DETAILED DESCRIPTION OF THE PREFERRED EMBODIMENTS

OUTLINE

I. General

II. Nucleic Acids

A. natural isolates; methods

B. synthetic genes

C. methods to isolate

III. Purified DX1 protein

A. physical properties

B. biological properties

IV. Making DX1 protein; Mimetics

A. recombinant methods

B. synthetic methods

C. natural purification

V. Physical Variants

A. sequence variants, fragments

B. post-translational variants 1. glycosylation 2. others

VI. Functional Variants
  A. analogues; fragments
    1. agonists
    2. antagonists
  B. mimetics
    1. protein
    2. chemicals
  C. species variants
VII. Antibodies
  A. polyclonal
  B. monoclonal
  C. fragments, binding compositions
VIII. Uses
  A. diagnostic
  B. therapeutic
IX. Kits
  A. nucleic acid reagents
  B. protein reagents
  C. antibody reagents
X. Methods for Isolating DX1 Specific Binding Partners I. General The present invention provides DNA sequence encoding various mammalian proteins which exhibit properties characteristic of functionally significant NK and T cell expressed molecules. The cDNA sequence exhibits various features which are characteristic of mRNAs encoding physiologically and developmentally important cell markers. See, e.g., Yokoyama (1993) *Ann. Rev. Immunol.* 11:613–35. The human gene described herein contains an open reading frame encoding a presumptive 226 amino acid protein. The protein is structurally related to a rat family of NK Receptor proteins (NKR-P) and mouse NK proteins. As such, the DX1 protein cloned herein likely represents one member of a class of related genes.

These proteins are designated DX1 proteins. The natural proteins should be capable of mediating various physiological responses which would lead to biological or physiological responses in target cells. Initial studies had localized this protein to various hematopoietic cell types. See, e.g., Table 0. Biochemical properties are described in Table 00.

TABLE 0

Distribution of DX1 markers.

60–99% of human peripheral blood $CD3^-56^+$ NK cells
<0.2% fetal and postnatal thymocytes
<2% cord blood T cells
~20% adult T cells, including CD4 and CD8 $\alpha\beta$-TcR and $\gamma\delta$-TcR T cells; correlated with "memory" subset
not detected on B cells, monocytes, or granulocytes

TABLE 00

Biochemical Properties of DX1 markers.

disulfide-linked homodimer 80 kD non-reduced; 40 kD subunits
complex and high mannose carbohydrates
core protein ~28 kD
no serine or tyrosine phosphorylation detected II. Nucleic Acids Table 1 discloses the nucleotide and amino acid sequences of one protein of the DX1 family. The described nucleotide sequences and the related reagents are useful in constructing a DNA clone useful for expressing DX1 protein, or, e.g., isolating a homologous gene from another natural source, including other members of the family. Typically, the sequences will be useful in isolating other genes, e.g., allelic variants or alternatively spliced isoforms, from human.

TABLE 1

Nucleotide sequence encoding a human DX1 protein and predicted amino acid sequence. Also can use complementary nucleic acid sequences for many purposes. A transmembrane segment appears to extend from amino acid 40 (ala) to amino acid 62 (val), with the amino proximal portion the intracellular segment, and the carboxy proximal portion the extracellular segment. SEQ ID NO: 1 and 2.

```
           10         20         30         40         50
AAAGCAGAAT TGAGAGTTTG TTCTTACACA CAAGTTTAAT GCCACCTTCC 60         69         78         87
TCTGTCTGCC ATG GAC CAA CAA GCA ATA TAT GCT GAG TTA
           MET Asp Gln Gln Ala Ile Tyr Ala Glu Leu 96        105        114        123
AAC TTA1 CCC ACA GAC TCA GGC CCA GAA AGT TCT TCA CCT
Asn Leu  Pro Thr Asp Ser Gly Pro Glu Ser Ser Ser Pro 132        141        150        159        168
TCA TCT CTT CCT CGG GAT GTC TGT CAG GGT TCA CCT TGG
Ser Ser Leu Pro Arg Asp Val Cys Gln Gly Ser Pro Trp 177        186        195        204
CAT CAA TTT GCC CTG AAA CTT AGC TGT GCT GGG ATT ATT
His Gln Phe Ala Leu Lys Leu Ser Cys Ala Gly Ile Ile 213        222        231        240
CTC CTT GTC TTG GTT GTT ACT GGG TTG AGT GTT TCA GTG
Leu Leu Val Leu Val Val Thr Gly Leu Ser Val Ser Val 249        258        267        276        285
```

TABLE 1-continued

Nucleotide sequence encoding a human DX1 protein and predicted amino acid sequence. Also can use complementary nucleic acid sequences for many purposes. A transmembrane segment appears to extend from amino acid 40 (ala) to amino acid 62 (val), with the amino proximal portion the intracellular segment, and the carboxy proximal portion the extracellular segment. SEQ ID NO: 1 and 2.

```
ACA TCC TTA ATA CAG AAA TCA TCA ATA GAA AAA TGC AGT
Thr Ser Leu Ile Gln Lys Ser Ser Ile Glu Lys Cys Ser 294         303         312         321
GTG GAC ATT CAA CAG AGC AGG AAT AAA ACA ACA GAG AGA
Val Asp Ile Gln Gln Ser Arg Asn Lys Thr Thr Glu Arg 330         339         348         357
CCG GGT CTC TTA AAC TGC CCA ATA TAT TGG CAG CAA CTC
Pro Gly Leu Leu Asn Cys Pro Ile Tyr Trp Gln Gln Leu 366         375         384         393         402
CGA GAG AAA TGC TTG TTA TTT TCT CAC ACT GTC AAC CCT
Arg Glu Lys Cys Leu Leu Phe Ser His Thr Val Asn Pro 411         420         429         438
TGG AAT AAC AGT CTA GCT GAT TGT TCC ACC AAA GAA TCC
Trp Asn Asn Ser Leu Ala Asp Cys Ser Thr Lys Glu Ser 447         456         465         474
AGC CTG CTG CTT ATT CGA GAT AAG GAT GAA TTG ATA CAC
Ser Leu Leu Leu Ile Arg Asp Lys Asp Glu Leu Ile His 483         492         501         510         519
ACA CAG AAC CTG ATA CGT GAC AAA GCA ATT CTG TTT TGG
Thr Gln Asn Leu Ile Arg Asp Lys Ala Ile Leu Phe Trp 528         537         546         555
ATT GGA TTA AAT TTT TCA TTA TCA GAA AAG AAC TGG AAG
Ile Gly Leu Asn Phe Ser Leu Ser Glu Lys Asn Trp Lys 564         573         582         591
TGG ATA AAC GGC TCT TTT TTA AAT TCT AAT GAC TTA GAA
Trp Ile Asn Gly Ser Phe Leu Asn Ser Asn Asp Leu Glu 600         609         618         627         636
ATT AGA GGT GAT GCT AAA GAA AAC AGC TGT ATT TCC ATC
Ile Arg Gly Asp Ala Lys Glu Asn Ser Cys Ile Ser Ile 645         654         663         672
TCA CAG ACA TCT GTG TAT TCT GAG TAC TGT AGT ACA GAA
Ser Gln Thr Ser Val Tyr Ser Glu Tyr Cys Ser Thr Glu 681         690         699         708
ATC AGA TGG ATC TGC CAA AAA GAA CTA ACA CCT GTG AGA
Ile Arg Trp Ile Cys Gln Lys Glu Leu Thr Pro Val Arg 717         726         735
AAT AAA GTG TAT CCT GAC TCT TGA
Asn Lys Val Tyr Pro Asp Ser
```

The purified protein or defined peptides are useful for generating antibodies by standard methods, as described above. Synthetic peptides or purified protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press.

For example, the specific binding composition could be used for screening of an expression library made from a cell line which expresses a DX1 protein. The screening can be standard staining of surface expressed protein, or by panning. Screening of intracellular expression can also be performed by various staining or immunofluorescence procedures. The binding compositions could be used to affinity purify or sort out cells expressing the protein.

This invention contemplates use of isolated DNA or fragments to encode a biologically active DX1 protein or polypeptide. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence as disclosed in Table 1. Further, this invention covers the use of isolated or recombinant DNA, or fragments thereof, which encode proteins which are homologous to a DX1 protein or which were isolated using cDNA encoding a DX1 protein as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule. Alternatively, a purified species may be separated from host components from a recombinant expression system.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by enetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A DNA which codes for a DX1 protein will be particularly useful to identify genes, mRNA, and cDNA species which code for related or homologous proteins, as well as DNAs which code for homologous proteins. There are likely homologues in other primates. Various DX1 proteins should be homologous and are encompassed herein. However, even proteins that have a more distant evolutionary relationship to the antigen can readily be isolated under appropriate conditions using these sequences if they are sufficiently homologous. Primate DX1 proteins are of particular interest.

This invention further covers recombinant DNA molecules and fragments having a DNA sequence identical to or highly homologous to the isolated DNAS set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180–199; each of which is incorporated herein by reference.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 1. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213, which is incorporated herein by reference. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370, which is hereby incorporated herein by reference.

III. Purified DX1 Protein

The predicted sequence of human DX1 amino acid sequence is shown in Table 1. The peptide sequences allow preparation of peptides to generate antibodies to recognize such segments, As used herein, DX1 shall encompass, when used in a protein context, a protein having amino acid sequences shown in Table 1, or a significant fragment of such a protein. It also refers to a primate, e.g., human, derived polypeptide which exhibits similar biological function or interacts with DX1 protein specific binding components. These binding components, e.g., antibodies, typically bind to a DX1 protein with high affinity, e.g., at least about 100 nM, usually better than about 30 nM, preferably better than about 10 nM, and more preferably at better than about 3 nM.

The term polypeptide, as used herein, includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids.

Substantially pure, in the polypeptide context, typically means that the protein is free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. The analysis may be weight or molar percentages, evaluated, e.g., by gel staining, spectrophotometry, or terminus labeling.

A binding composition refers to molecules that bind with specificity to DX1 protein, e.g., in a ligand-receptor type fashion, an antibody-antigen interaction, or compounds, e.g., proteins which specifically associate with DX1 protein, e.g., in a natural physiologically relevant protein—protein interaction, either covalent or non-covalent. The molecule may be a polymer, or chemical reagent. No implication as to whether DX1 protein is either the ligand or the receptor of a ligand-receptor interaction is represented, other than the interaction exhibit similar specificity, e.g., specific affinity. A functional analog may be a protein with structural modifications, or may be a wholly unrelated molecule, e.g., which has a molecular shape which interacts with the appropriate binding determinants. The proteins may serve as agonists or antagonists of a receptor, see, e.g., Goodman et al. (eds.) (1990) *Goodman & Gilman's: The Pharmacological Bases of Therapeutics* (8th ed.), Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the antigen.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco; each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

IV. Making DX1 Protein; Mimetics

DNA which encodes the DX1 protein or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length protein or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a DX1 protein, or a fragment thereof, typically encoding a biologically active polypeptide. The DNA can be under the control of a viral promoter and can encode a selection marker. This invention further contemplates use of such expression vectors which are capable of expressing eukaryotic cDNA coding for a DX1 protein in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of a DX1 gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels et al. (1985 and Supplements) *Cloning vectors: A Laboratory Manual*, Elsevier, N.Y., and Rodriquez et al. (1988)(eds.) *Vectors: A Survey of Molecular Cloning vectors and Their Uses*, Buttersworth, Boston, Mass., which are incorporated herein by reference.

Transformed cells include cells, preferably mammalian, that have been transformed or transfected with vectors containing a DX1 gene, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the DX1 proteins or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236, which is incorporated herein by reference.

Lower eukaryotes, e.g., yeasts and Dictyostelium, may be transformed with vectors encoding DX1 proteins. For purposes of this invention, the most common lower eukaryotic host is the bakers yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active DX1 protein. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama et al. (1985) *Mol. Cell Biol.* 5:1136–1142; pMC1neo Poly-A, see Thomas et al. (1987) *Cell* 51:503–512; and a baculovirus vector such as pAC 373 or pAC 610.

It will often be desired to express a DX1 protein polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the DX1 protein gene may be co-transformed with one or more genes encoding mammalian or other glycosylating enzymes. Using this approach, certain mammalian glycosylation patterns will be achievable or approximated in prokaryote or other cells.

The DX1 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse et al. (1985) *Science* 230:1003–1008; and Brunner et al. (1991) *J. Cell Biol.* 114:1275–1283.

Now that the DX1 protein has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; all of each are incorporated herein by reference. For example, an azide process, an acid chloride process, an acid anhydride process, a mixed anhydride process, an active ester process (for example, p-nitrophenyl ester, N-hydroxysuccinimlde ester, or cyanomethyl ester), a carbodiimidazole process, an oxidative-reductive process, or a dicyclohexylcarbodiimide (DCCD)/ additive process can be used. Solid phase and solution phase syntheses are both applicable to the foregoing processes.

The DX1 protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield et al. (1963) in *J. Am. Chem. Soc.* 85:2149–2156, which is incorporated herein by reference.

The prepared protein and fragments thereof can be isolated and purified from the reaction mixture by means of peptide separation, for example, by extraction, precipitation, electrophoresis and various forms of chromatography, and the like. The DX1 proteins of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the DX1 protein as a result of DNA techniques, see below.

V. Physical Variants

This invention also encompasses proteins or peptides having substantial amino acid sequence homology with the amino acid sequence of the DX1 protein. The variants include species and allelic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the DX1 protein. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham et al. (1970) *J. Mol. Biol.* 48:443–453; Sankoff et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.; each of which is incorporated herein by reference.

The isolated DNA encoding a DX1 protein can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant DX1 protein derivatives include predetermined or site-specific mutations of the respective protein or its fragments. "Mutant DX1 protein" encompasses a polypeptide otherwise falling within the homology definition of the human DX1 protein as set forth above, but having an amino acid sequence which differs from that of DX1 protein as found in nature, whether by way of deletion, substitution, or insertion. In particular, "site specific mutant DX1 protein" generally includes proteins having significant homology with a protein having sequences of Table 1, and as sharing various biological activities, e.g., antigenic or immunogenic, with those sequences, and in preferred embodiments contain most of the disclosed sequences. Similar concepts apply to different DX1 proteins, particularly those found in various mammals, e.g., primates, including human. AS stated before, it is emphasized that descriptions are generally meant to encompass all DX1 proteins, not limited to the specific embodiment discussed.

Although site specific mutation sites are predetermined, mutants need not be site specific. DX1 protein mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook et al. (1989) and Ausubel et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a DX1 polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, antigen-binding or other segments may be "swapped" between different new fusion polypeptides or fragments. See, e.g., Cunningham et al. (1989) Science 243:1330–1336; and O'Dowd et al. (1988) J. Biol. Chem. 263:15985–15992, each of which is incorporated herein by reference. Thus, new chimeric polypeptides exhibiting new combinations of specificities will result from the functional linkage of biologically relevant domains and other functional domains.

The phosphoramidite method described by Beaucage and Carruthers (1981) Tetra. Letts. 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

VI. Functional Variants

The blocking of physiological response to DX1 proteins may result from the inhibition of binding of the antigen to its natural binding partner, e.g., through competitive inhibition. Thus, in vitro assays of the present invention will often use isolated protein, membranes from cells expressing a recombinant membrane associated DX1 protein, soluble fragments comprising binding segments, or fragments attached to solid phase substrates. These assays will also allow for the diagnostic determination of the effects of either binding segment mutations and modifications, or protein mutations and modifications, e.g., analogues. In particular, the DX1 is stably expressed on NK clones, but the antigen is lost after T cell activation (T cell clones are negative).

This invention also contemplates the use of competitive drug screening assays, e.g., where neutralizing antibodies to antigen or binding partner fragments compete with a test compound for binding to the protein. In this manner, the antibodies can be used to detect the presence of any polypeptide which shares one or more antigenic binding sites of the protein and can also be used to occupy binding sites on the protein that might otherwise interact with a binding partner.

Additionally, neutralizing antibodies against the DX1 protein and soluble fragments of the antigen which contain a high affinity receptor binding site, can be used to inhibit antigen function in tissues, e.g., tissues experiencing abnormal physiology.

"Derivatives" of the DX1 antigens include amino acid sequence mutants, glycosylation variants, and covalent or aggregate conjugates with other chemical moieties. Covalent derivatives can be prepared by linkage of functionalities to groups which are found in the DX1 amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the DX1 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred antigen derivatization sites with cross-linking agents are at free amino groups, carbohydrate moieties, and cysteine residues.

Fusion polypeptides between the DX1 proteins and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of an antigen, e.g., a receptor-binding segment, so that the presence or location of the fused antigen may be easily determined. See, e.g., Dull et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook et al. (1989) *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield (1963) *J. Amer. Chem. Soc.* 85:2149–2156; Merrifield (1986) *Science* 232: 341–347; and Atherton et al. (1989) *Solid Phase Peptide Synthesis: A Practical Approach*, IRL Press, Oxford; each of which is incorporated herein by reference.

This invention also contemplates the use of derivatives of the DX1 proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of antigens or other binding proteins. For example, a DX1 antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-DX1 protein antibodies or its receptor or other binding partner. The DX1 antigens can also be labeled with a detectable group, for example radioiodinated by the chloramine T procedure, covalently bound to rare earth chelates, or conjugated to another fluorescent moiety for use in diagnostic assays. Purification of DX1 protein may be effected by immobilized antibodies or binding partners.

A solubilized DX1 antigen or fragment of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, the term "antibodies" also encompasses antigen binding fragments of natural antibodies. The purified DX1 proteins can also be used as a reagent to detect any antibodies generated in response to the presence of elevated levels of the protein or cell fragments containing the antigen, both of which may be diagnostic of an abnormal or specific physiological or disease condition. Additionally, antigen fragments may also serve as immunogens to produce the antibodies of the present invention, as described immediately below. For example, this invention contemplates antibodies raised against amino acid sequences encoded by nucleotide sequences shown in Table 1, or fragments of proteins containing them. In particular, this invention contemplates antibodies having binding affinity to or being raised against specific fragments which are predicted to lie outside of the lipid bilayer.

The invention also provides means to isolate a group of related antigens displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species.

The isolated genes will allow transformation of cells lacking expression of a corresponding DX1 protein, e.g., either species types or cells which lack corresponding antigens and should exhibit negative background activity. Expression of transformed genes will allow isolation of antigenically pure cell lines, with defined or single specie variants. This approach will allow for more sensitive detection and discrimination of the physiological effects of DX1 proteins. Subcellular fragments, e.g., cytoplasts or membrane fragments, can be isolated and used.

Dissection of the critical structural elements which effect the various physiological or differentiation functions provided by the proteins is possible using standard techniques of modern molecular biology, particularly in comparing members of the related class. See, e.g., the homolog-scanning mutagenesis technique described in Cunningham et al. (1989) *Science* 243:1339–1336; and approaches used in O'Dowd et al. (1988) *J. Biol. Chem.* 263:15985–15992; and Lechleiter et al. (1990) *EMBO J.* 9:4381–4390; each of which is incorporated herein by reference.

In particular, functional domains or segments can be substituted between species variants or related proteins to determine what structural features are important in both binding partner affinity and specificity, as well as signal transduction. An array of different variants will be used to screen for molecules exhibiting combined properties of interaction with different species variants of binding partners.

Antigen internalization may occur under certain circumstances, and interaction between intracellular components and extracellular segments of proteins involved in interactions may occur. The specific segments of interaction of DX1 protein with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of DX1 protein will be pursued. The controlling elements associated with the antigens may exhibit differential developmental, tissue specific, or other expression patterns. Upstream or downstream genetic regions, e.g., control elements, are of interest.

Structural studies of the antigen will lead to design of new variants, particularly analogues exhibiting agonist or antagonist properties on binding partners. This can be combined with previously described screening methods to isolate variants exhibiting desired spectra of activities.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Thus, the present invention provides important reagents related to antigen-binding partner interaction. Although the foregoing description has focused primarily upon the human DX1 protein, those of skill in the art will immediately recognize that the invention encompasses other closely related antigens, e.g., other primate species or allelic variants, as well as variants and other members of the family.

VII. Antibodies

Antibodies can be raised to the various DX1 proteins, including species or allelic variants, and fragments thereof, both in their naturally occurring forms and in their recombinant forms. Additionally, antibodies can be raised to DX1 proteins in either their active forms or in their inactive forms. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective DX1 proteins, or screened for agonistic or antagonistic activity, e.g., mediated through a binding partner. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

The antibodies, including antigen binding fragments, of this invention can have significant diagnostic or therapeutic value. They can be potent antagonists that bind to a binding partner and inhibit antigen binding or inhibit the ability of an antigen to elicit a biological response. They also can be useful as non-neutralizing antibodies and can be coupled to toxins or radionuclides so that when the antibody binds to the antigen, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying DX1 protein or its binding partners.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams et al. (1967) *Methods in Immunology and Immunochemistry*, Vol. 1, Academic Press, New York, each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse et al. (1989) "Generation of a Large Combinatorial Library of the Immunoglobulin Repertoire in Phage Lambda," *Science* 246:1275–1281; and Ward et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241. Also, recombinant immunoglobulins may be produced, see Cabilly, U.S. Pat. No. 4,816,567. These patents are incorporated herein by reference.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified DX1 protein will be released.

The antibodies may also be used to screen expression libraries for particular expression products. Usually the antibodies used in such a procedure will be labeled with a moiety allowing easy detection of presence of antigen by antibody binding.

Antibodies raised against each DX1 protein will also be useful to raise anti-idiotypic antibodies. These will be useful in detecting or diagnosing various immunological conditions related to expression of the respective antigens.

VIII. Uses

The present invention provides reagents which will find use in diagnostic applications as described elsewhere herein, e.g., in the general description for physiological or developmental abnormalities, or below in the description of kits for diagnosis.

This invention also provides reagents with significant therapeutic value. The DX1 protein (naturally occurring or recombinant), fragments thereof, and antibodies thereto, along with compounds identified as having binding affinity to DX1 protein, should be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a DX1 antigen should be a likely target for an agonist or antagonist of the protein.

Other abnormal developmental conditions are known in the cell types shown to possess DX1 antigen mRNA by Northern blot analysis. See Berkow (ed.) *The Merck Manual of Diagnosis and Therapy*, Merck & Co., Rahway, N.J.; and Thorn et al. *Harrison's Principles of Internal Medicine*, McGraw-Hill, N.Y. These problems may be susceptible to prevention or treatment using compositions provided herein.

Recombinant antibodies which bind to DX1 can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Screening using DX1 for binding partners or compounds having binding affinity to DX1 antigen can be performed, including isolation of associated components. Subsequent biological assays can then be utilized to determine if the compound has intrinsic biological activity and is therefore an agonist or antagonist in that it blocks an activity of the antigen. This invention further contemplates the therapeutic use of antibodies to DX1 protein as antagonists. This approach should be particularly useful with other DX1 protein species variants and other members of the family.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds.) (1990) *Goodman and Gilman's: The Pharmacological Bases of Therapeutics*, 8th Ed., Pergamon Press; and *Reminaton's Pharmaceutical Sciences*, 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

DX1 protein, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. The therapy of this invention may be combined with or used in association with other chemotherapeutic or chemopreventive agents.

Both the naturally occurring and the recombinant form of the DX1 proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor et al. (1991) *Science* 251:767–773, which is incorporated herein by reference and which describes means for testing of binding affinity by a plurality of defined polymers synthesized on a solid substrate. The development of suitable assays can be greatly facilitated by the availability of large amounts of purified, soluble DX1 protein as provided by this invention.

This invention is particularly useful for screening compounds by using recombinant antigen in any of a variety of drug screening techniques. The advantages of using a recombinant protein in screening for specific ligands include: (a) improved renewable source of the antigen from a specific source; (b) potentially greater number of antigen molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology*; Hood et al. *Immunology* Benjamin/Cummings; Paul (ed.) *Fundamental Immunology*; and *Methods in Enzymology* Academic Press. This will also be useful in screening for a ligand which binds a DX1, e.g., from an interacting cell.

One method of drug screening utilizes eukaryotic or prokaryotic host cells which are stably transformed with recombinant DNA molecules expressing the DX1 antigens. Cells may be isolated which express an antigen in isolation from other functionally equivalent antigens. Such cells, either in viable or fixed form, can be used for standard protein—protein binding assays. See also, Parce et al. (1989) *Science* 246:243–247; and Owicki et al. (1990) *Proc. Nat'l Acad. Sci. USA* 87:4007–4011, which are incorporated herein by reference and describe sensitive methods to detect cellular responses. Competitive assays are particularly useful, where the cells (source of DX1 protein) are contacted and incubated with a labeled binding partner or antibody having known binding affinity to the ligand, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled receptor binding to the known source. Any one of numerous techniques can be used to separate bound from free antigen to assess the degree of binding. This separation step could typically involve a procedure such as adhesion to filters followed by washing, adhesion to plastic followed by washing, or centrifugation of the cell membranes. Viable cells could also be used to screen for the effects of drugs on DX1 protein mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the DX1 protein. These cells are stably transformed with DNA vectors directing the expression of a membrane associated DX1 protein, e.g., an engineered membrane bound form. Essentially, the membranes would be prepared from the cells and used in any receptor/ligand type binding assay such as the competitive assay set forth above.

Still another approach is to use solubilized, unpurified or solubilized, purified DX1 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to DX1 and is described in detail in Geysen, European Patent Application 84/03564, published on Sep. 13, 1984, which is incorporated herein by reference. First, large numbers of different small peptide test compounds are synthesized on a solid substrate, e.g., plastic pins or some other appropriate surface, see Fodor et al. (1991). Then all the pins are reacted with solubilized, unpurified or solubilized, purified DX1 binding composition, and washed. The next step involves detecting bound binding composition.

Rational drug design may also be based upon structural studies of the molecular shapes of the DX1 protein and other effectors or analogues. Effectors may be other proteins which mediate other functions in response to antigen binding, or other proteins which normally interact with the antigen, e.g., DX1 ligand. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

Purified DX1 protein can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of DX1 proteins, fragments thereof, peptides, and their fusion products in a variety of diagnostic kits and methods for detecting the presence of a binding composition. Typically the kit will have a compartment containing either a defined DX1 peptide or gene segment or a reagent which recognizes one or the other, e.g., antigen fragments or antibodies.

A kit for determining the binding affinity of a test compound to a DX1 protein would typically comprise a test compound; a labeled compound, for example an antibody having known binding affinity for the antigen; a source of DX1 protein (naturally occurring or recombinant); and a means for separating bound from free labeled compound, such as a solid phase for immobilizing the antigen. Once compounds are screened, those having suitable binding affinity to the antigen can be evaluated in suitable biological assays, as are well known in the art, to determine whether they exhibit similar biological activities to the natural antigen. The availability of recombinant DX1 protein polypeptides also provide well defined standards for calibrating such assays.

A preferred kit for determining the concentration of, for example, a DX1 protein in a sample would typically comprise a labeled compound, e.g., antibody, having known binding affinity for the antigen, a source of antigen (naturally occurring or recombinant) and a means for separating the bound from free labeled compound, for example, a solid phase for immobilizing the DX1 protein. Compartments containing reagents, and instructions, will normally be provided.

One method for determining the concentration of DX1 protein in a sample would typically comprise the steps of: (1) preparing membranes from a sample comprised of a membrane bound DX1 protein source; (2) washing the membranes and suspending them in a buffer; (3) solubilizing the antigen by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the DX1 protein or fragments are useful in diagnostic applications to detect the presence of elevated levels of DX1 protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and protein—protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a DX1 protein or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against a DX1 protein, as such may be diagnostic of various abnormal states. For example, overproduction of DX1 protein may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled DX1 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the antigen, test compound, DX1 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free antigen, or alternatively the bound from the free test compound. The DX1 protein can be immobilized on various matrixes followed by washing. Suitable matrixes include plastic such as an ELISA plate, filters, and beads. Methods of immobilizing the DX1 protein to a matrix include, without limitation, direct adhesion to plastic, use of a capture antibody, chemical coupling, and biotin-avidin. The last step in this approach involves the precipitation of protein—protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle et al. (1984) *Clin. Chem.* 30:1457–1461, and the double antibody magnetic particle separation as described in U.S. Pat. No. 4,659,678, each of which is incorporated herein by reference.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a DX1 protein. These sequences can be used as probes for detecting levels of antigen message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet et al. (1989) *Progress in Growth Factor Res.* 1:89–97.

X. Methods for Isolating DX1 Specific Binding Partners

The DX1 protein should interact with a ligand based, e.g., upon its similarity in structure and function to other cell markers exhibiting developmental and cell type specificity of expression. Methods to isolate a ligand are made available by the ability to make purified DX1 for screening programs. Soluble or other constructs using the DX1 sequences provided herein will allow for screening or isolation of DX1 specific ligands.

The broad scope of this invention is best understood with reference to the following examples, which are not intended to limit the invention to specific embodiments.

EXAMPLES

I. General Methods

Some of the standard methods are described or referenced, e.g., in Maniatis et al. (1982) *Molecular Cloning, A Laboratory Manual*, Cold Spring Harbor Laboratory, Cold Spring Harbor Press; Sambrook et al. (1989) *Molecular Cloning: A Laboratory Manual*, (2d ed.), vols 1–3, CSH Press, NY; Ausubel et al., *Biology*, Greene Publishing Associates, Brooklyn, N.Y.; or Ausubel et al. (1987 and Supplements) *Current Protocols in Molecular Biology*, Greene/Wiley, New York; Innis et al. (eds.)(1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif.; which are incorporated herein by reference. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe et al. (1992) *QIAexpress: The High Level Expression & Protein Purification System* QUIAGEN, Inc., Chatsworth, Calif.: which are incorporated herein by reference.

FACS analyses are described in Melamed et al. (1990) *Flow Cytometry and Sorting* Wiley-Liss, Inc., New York, N.Y.; Shapiro (1988) *Practical Flow Cytometry Liss*, New York, N.Y.; and Robinson et al. (1993) *Handbook of Flow Cytometry Methods* Wiley-Liss, New York, N.Y.

II. Preparation of a Monoclonal Antibody.

Balb/c mice were immunized with human peripheral blood NK cells cultured in medium containing interleukin-2. Splenocytes were fused with the Sp2/0 fusion partner and hybridomas were selected in growth medium containing azaserine by standard procedures. The original anti-DX1 antibody is an IgG1,k mAb.

III. Distribution of DX1 Antigen.

DX1 antigen is expressed on ~60–99% of human peripheral blood CD3-56+ NK cells (varies depending on the donor). Most fetal and cord blood NK cells also express DX1, whereas DX1 is only expressed on a minor proportion (<10%) of fetal T cells, cord blood T cells, or thymocytes. In human adult peripheral blood, ~20% of CD3+ T cells express DX1, including both CD4 and CD8 T cells in varying proportions. Both $\alpha\beta$-TcR and $\gamma\delta$-TcR bearing T cells can express DX1. In general, DX1 is preferentially expressed on "memory" T cells, identified by co-expression of CD45RO or fas antigen, in adult peripheral blood. DX1 was not detected on resting human granulocytes or monocytes. After in vitro activation with PHA, DX1 is lost on T cells, but is maintained in vitro on IL-2 activated NK cells and NK cell clones.

IV. Biochemical Characterization of DX1.

Anti-DX1 antibody recognizes a disulfide-linked homodimer glycoprotein (MW ~80 kD non-reducing; ~40 kD reducing) on human T cells and NK cells, based on 2 dimensional (non-reduced/reduced) SDS-PAGE analysis. Removal of N-linked oligosaccharides revealed an ~27–28 kD protein. Both high mannose and complex N-linked oligosaccharides were present, based on susceptibility to endo H and N-glycanase cleavage, respectively. In theory, it is possible that disulfide-linked heterodimers may exist between different DX1 family members.

III. Isolation of a DNA Clone Encoding DX1 Protein.

DX1 antigen was expression cloned from a polyclonal human activated NK cell cDNA library in the pJFE14 expression vector. COS7 cells were transfected with the library and antigen positive cells were selected using phycoerythrin labeled anti-DX1 mAb. The cDNA sequence revealed a type II membrane protein with a predicted MW of 25.5 kD, similar to the expected size based on prior biochemical analysis. The gene is on human chromosome 12. The sequence revealed similarity to the rat and mouse NKR-P1 gene family and suggested that DX1 is a human NKR-P1 homologue. These proteins are members of the animal C-lectin family, suggesting possible carbohydrate ligands, although not excluding protein ligands. Known human cell surface antigens with C-lectin motifs include human NKG2, mouse Ly49, human and rat NKR-P1, human CD23, human CD69, human CD62, human E-selectin, human L-selectin, rat Kupffer cell receptor, and human asialoglycoprotein receptor.

In another method, oligonucleotides are used to screen a library. In combination with polymerase chain reaction (PCR) techniques, synthetic oligonucleotides in appropriate orientations are used as primers to select correct clones from a library.

Biochemical Characterization of the DX1 Protein.

A recombinant DX1 construct is prepared which is fused to a useful affinity reagent, e.g., FLAG peptide, useful for purifying the expression product of the construct. See, e.g., Crowe et al. (1992) *QIAexpress: The High Level Expression & Protein Purification System* QUIAGEN, Inc. Chatsworth, Calif.; and Hopp et al. (1988) *Bio/Technology* 6:1204–1210. The sequence allows for efficient affinity purification of the soluble product. Appropriate secretion or processing sites may also be engineered into the construct by standard methods. Purification is achieved by use of affinity purification, e.g., antibodies against the antigen, or by standard protein purification methods. Typically, the affinity reagents or purification procedures can be performed using recombinant receptor.

Preparation of Antibodies Specific for DX1

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods.

Purification of the DX1 Protein

The DX1 protein is isolated by a combination of affinity chromatography using the DX1 specific binding compositions, e.g., antibody, as a specific binding reagent in combination with protein purification techniques allowing separation from other proteins and contaminants. Similar techniques using human cell assays and human cell sources are applied to isolate a human antigen.

The DX1 is used for screening of an expression library made from a cell line which expresses a DX1 binding protein, e.g., a ligand. Standard staining techniques are used to detect or sort intracellular or surface expressed ligand, or surface expressing transformed cells are screened by panning. Screening of intracellular expression is performed by various staining or immunofluorescence procedures. See also McMahan et al. (1991) *EMBO J*. 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at 2–3×10$^5$ cells per chamber in 1.5 ml of growth media. Incubate overnight at 37° C.

On day 1 for each sample, prepare 0.5 ml of a solution of 66 μg/ml DEAE-dextran, 66 μM chloroquine, and 4 μg DNA in serum free DME. For each set, a positive control is prepared, e.g., of huIL-10-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at ~80° C. after all liquid is removed. For each chamber, 0.5 ml incubations are performed as follows. Add HBSS/saponin (0.1%) with 32 μl/ml of 1M NaN$_3$ for 20 min. Cells are then washed with HBSS/saponin 1×. Soluble antibody is added to cells and incubate for 30 min. wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and pre-incubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85–90° C.

Alternatively, the DX1 proteins are used to affinity purify or sort out cells expressing the ligand. See, e.g., Sambrook et al. or Ausubel et al, which are incorporated herein by reference.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A composition selected from the group consisting of:
   a) a recombinant or isolated nucleic acid encoding at least 10 contiguous amino acids of SEQ ID NO: 2;
   b) a substantially pure polypeptide comprising at least 10 contiguous amino acids of SEQ ID NO: 2; and
   c) an antibody raised to a recombinant or purified primate DX1 protein.

2. A recombinant or isolated nucleic acid encoding at least 12 contiguous amino acids from a primate DX1 protein (see SEQ ID NO: 2).

3. The nucleic acid of claim 2, wherein said nucleic acid comprises at least 24 contiguous nucleotides from the coding portion of SEQ ID NO: 1.

4. A substantially pure polypeptide comprising at least 12 contiguous amino acids from a primate DX1 protein (see SEQ ID NO: 2).

5. The polypeptide of claim 4, selected from the group consisting of:
   a) a polypeptide from a human;
   b) a polypeptide comprising at least 14 contiguous amino acids from SEQ ID NO: 2; and
   c) an unglycosylated polypeptide.

6. A sterile composition comprising said polypeptide of claim 4.

7. An antibody raised to a recombinant or purified polypeptide of claim 4.

8. The antibody of claim 7, wherein:
   a) said DX1 protein is from human;
   b) said antibody is raised against SEQ ID NO: 2;
   c) said antibody is a monoclonal antibody; or
   d) said antibody is labeled.

9. A kit comprising said recombinant or isolated nucleic acid of claim 2 and;
   a) a compartment comprising said nucleic acid;
   b) instructions for use or disposal of reagents in said kit; or
   c) said compartment comprising said nucleic acid and instructions for use or disposal of reagents in said kit.

10. The kit of claim 9, wherein said nucleic acid comprises at least 24 continuous nucleotides from the coding portion of SEQ ID NO: 1.

11. A kit comprising said polypeptide of claim 5 and:
    i) a compartment comprising said polypeptide;
    ii) instructions for use or disposal of reagents in said kit; or
    iii) both i and ii.

12. A kit comprising said antibody of claim 8 and:
    i) a compartment comprising said polypeptide;
    ii) instructions for use or disposal of reagents in said kit; or
    iii) both i and ii.

13. A method of screening a sample for a ligand for DX1 comprising the steps of producing a purified or recombinant primate DX1 protein, and screening in said sample for a specific binding of said ligand to said DX1 protein.

14. A method of modulating physiology or development of a cell comprising contacting said cell with an agonist or antagonist of a primate DX1 protein.

15. The method of claim 14, wherein said antagonist is an antibody against a primate DX1 protein.

16. An isolated or recombinant nucleic acid comprising at least 35 contiguous nucleotides of the coding portion from SEQ ID NO: 1.

17. The nucleic acid of claim 16, comprising a portion of a primate DX1 gene encoding a sequence selected from the group consisting of:
    a) the intracellular segment of SEQ ID NO: 2;
    b) the transmembrane segment of SEQ ID NO: 2;
    c) the extracellular segment of SEQ ID NO: 2; and
    d) the entire mature DX1 from SEQ ID NO: 2.

18. A substantially pure polypeptide comprising at least 22 contiguous amino acids from SEQ ID NO: 2.

19. The polypeptide of claim 18, comprising a portion of DX1 selected from the group consisting of:
    a) the intracellular segment of SEQ ID NO: 2;
    b) the transmembrane segment of SEQ ID NO: 2;
    c) the extracellular segment of SEQ ID NO: 2; and
    d) the entire mature DX1 from SEQ ID NO: 2.

20. The method of claim 13, wherein said ligand is an antibody which binds specifically to a human DX1.

21. The composition of claim 1, which is the recombinant or isolated nucleic acid encoding at least 10 contiguous amino acids of SEQ ID NO: 2.

22. The nucleic acid of claim 21, which encodes at least 14 contiguous amino acids of SEQ ID NO: 2.

23. The nucleic acid of claim 22, which encodes at least 22 contiguous amino acids of SEQ ID NO: 2.

24. The composition of claim 1, which is the substantially pure polypeptide comprising at least 10 contiguous amino acids of SEQ ID NO: 2.

25. The polypeptide of claim 24, which comprises at least 14 contiguous amino acids of SEQ ID NO: 2.

26. The polypeptide of claim 25, which comprises at least 22 contiguous amino acids of SEQ ID NO: 2.

27. The composition of claim 1, which is the antibody raised to a recombinant or purified primate DX1 protein.

28. The antibody of claim 27, wherein;

a) said antibody is a polyclonal antibody; or b) said primate DX1 has the sequence of SEQ ID NO: 2.

* * * * *